(12) United States Patent
Teague et al.

(10) Patent No.: US 10,349,959 B2
(45) Date of Patent: Jul. 16, 2019

(54) MEDICAL RETRIEVAL DEVICES

(71) Applicant: Boston Scientific Scimed, Inc., Maple Grove, MN (US)

(72) Inventors: James A. Teague, Spencer, IN (US);
Eric Cheng, New Richmond, OH (US);
Jason W. Kear, Bloomington, IN (US);
Juli L. Curtis, Bloomington, IN (US);
Kevin R. Heath, Weston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 86 days.

(21) Appl. No.: 14/853,022

(22) Filed: Sep. 14, 2015

(65) Prior Publication Data

US 2016/0000451 A1 Jan. 7, 2016

Related U.S. Application Data

(63) Continuation of application No. 13/956,019, filed on Jul. 31, 2013, now Pat. No. 9,149,289, which is a continuation of application No. 11/812,096, filed on Jun. 14, 2007, now Pat. No. 8,518,054.

(60) Provisional application No. 60/860,216, filed on Nov. 21, 2006.

(51) Int. Cl.
*A61B 17/221* (2006.01)

(52) U.S. Cl.
CPC .................. *A61B 17/221* (2013.01)

(58) Field of Classification Search
CPC .......... A61B 17/221; A61B 2017/2212; A61B 2017/2215; A61B 2017/2217
See application file for complete search history.

(56) References Cited

U.S. PATENT DOCUMENTS

| 3,828,790 | A | | 8/1974 | Curtiss et al. |
| 4,994,079 | A | * | 2/1991 | Genese ............... A61B 17/221 |
| | | | | 606/206 |
| 5,522,819 | A | * | 6/1996 | Graves ............... A61B 17/221 |
| | | | | 606/110 |
| 5,906,594 | A | | 5/1999 | Scarfone et al. |

(Continued)

FOREIGN PATENT DOCUMENTS

| WO | WO 2004/093697 A1 | 11/2004 |
| WO | WO 2005/011506 A2 | 2/2005 |

OTHER PUBLICATIONS

International Preliminary Report on Patentability for International Application No. PCT/US2007/072236, dated Jun. 4, 2009.

*Primary Examiner* — Elizabeth Houston
*Assistant Examiner* — Sarah Simpson
(74) *Attorney, Agent, or Firm* — Bookoff McAndrews, PLLC

(57) ABSTRACT

A medical retrieval device of an embodiment of the present disclosure includes a proximal handle, a sheath, and a retrieval assembly. The sheath extends from the handle and includes a lumen and a distal end opposite the handle. The retrieval assembly is moveable relative to the sheath to achieve a collapsed position of the retrieval assembly within the lumen and an expanded position of the retrieval assembly when extended outside the lumen. The retrieval assembly includes a plurality of legs. At least one of the legs includes a wire having an inner core at least partially surrounded by an outer layer.

20 Claims, 14 Drawing Sheets

(56) References Cited

U.S. PATENT DOCUMENTS

| | | |
|---|---|---|
| 6,059,796 A | 5/2000 | Bilitz et al. |
| 6,090,129 A * | 7/2000 | Ouchi ................ A61B 17/221 |
| | | 606/113 |
| 6,344,049 B1 | 2/2002 | Levinson et al. |
| 6,368,328 B1 | 4/2002 | Chu et al. |
| 6,695,834 B2 | 2/2004 | Gellman et al. |
| 6,743,237 B2 | 6/2004 | Dhindsa |
| 6,939,349 B2 | 9/2005 | Fleischman et al. |
| 2002/0121472 A1 | 9/2002 | Garner et al. |
| 2002/0133170 A1 | 9/2002 | Tsuruta |
| 2003/0153843 A1 | 8/2003 | Nishtalas et al. |
| 2004/0199200 A1 | 10/2004 | Teague et al. |
| 2004/0215212 A1 | 10/2004 | Teague et al. |
| 2004/0220609 A1 | 11/2004 | Douk et al. |
| 2005/0049612 A1 | 3/2005 | Urbanski et al. |
| 2005/0119668 A1* | 6/2005 | Teague ................ A61B 17/221 |
| | | 606/127 |
| 2005/0154378 A1* | 7/2005 | Teague ................ A61B 17/221 |
| | | 606/2.5 |
| 2006/0052797 A1 | 3/2006 | Kanamaru |
| 2006/0129166 A1 | 6/2006 | Lavelle |
| 2007/0179507 A1 | 8/2007 | Shah |
| 2007/0208350 A1* | 9/2007 | Gunderson ............... A61F 2/95 |
| | | 606/108 |
| 2007/0299456 A1 | 12/2007 | Teague |

* cited by examiner

MEDICAL RETRIEVAL DEVICES

PRIORITY DATA

This application is a continuation of U.S. patent application Ser. No. 13/956,019, filed Jul. 31, 2013, which is a continuation of U.S. patent application Ser. No. 11/812,096, filed Jun. 14, 2007, now U.S. Pat. No. 8,518,054, which claims the benefit of priority from U.S. Provisional Patent Application No. 60/860,216, filed Nov. 21, 2006, all of which are incorporated herein by reference in their entirety.

FIELD OF THE INVENTION

This disclosure relates generally to medical devices and more particularly to medical retrieval devices.

BACKGROUND OF THE INVENTION

Medical extractors have been used for the removal of various bodily tissue, including stones or calculi, or other foreign objects, from within the body. One type of extractor has a basket connected to the distal end of a wire. The extractor may also include a sheath that is moveable relative to the basket and the wire, and the basket may include a number of legs. The basket may be deployed as the sheath is withdrawn from the legs and may be collapsed as the sheath is extended over the legs. Once the basket is deployed, a targeted stone may be captured within the basket. The device may further include a proximal handle and a slide, connected to the sheath and wire, for deploying and collapsing the basket.

The effectiveness of a stone retrieval device may depend on the desired balance between basket flexibility and basket strength. Conventional baskets may include elements made solely of one material. Such elements may have the same strength, flexibility, or other mechanical characteristics throughout, making it difficult to achieve this balance. For example, basket legs made of steel may be relatively strong and rigid, but may be relatively inflexible as compared to legs made from other more pliable materials. On the other hand, basket legs made of nitinol may be relatively more flexible, but exhibit less strength. Thus, baskets or other parts of a medical retrieval device made from elements composed of a single material may suffer from the mechanical disadvantages of the material used to form the elements.

The present disclosure provides medical retrieval devices that avoid some of the aforementioned shortcomings of existing devices.

SUMMARY OF THE INVENTION

In accordance with an aspect of the present disclosure, a medical retrieval device includes a proximal handle, a sheath extending from the handle and including a lumen and a distal end opposite the handle, and a retrieval assembly that is moveable relative to the sheath. The retrieval assembly achieves a collapsed position of the retrieval assembly within the lumen and an expanded position of the retrieval assembly when extended outside the lumen. The retrieval assembly includes a plurality of legs, at least one of the legs including a wire having an inner core at least partially surrounded by an outer layer.

Embodiments of the medical device may include one or more of the following features. The inner core is comprised of a first material and the outer layer is comprised of a second material that is more rigid than the first material. The first material is nitinol and the second material is stainless steel. The outer layer has a varying cross-section along the wire. The outer layer defines at least one void exposing the inner core. The void extends around a circumference of the wire. The void is spiral shaped. The void extends only partially around a circumference of the wire. The void is positioned at an inner surface of the wire. The void is formed by removing a portion of the outer layer. The portion of the outer layer is removed by etching or grinding. The plurality of legs join at a proximal end of the retrieval assembly, and the void is positioned at the proximal end of the retrieval assembly. An over-cannula of the device is positioned at the void to join the plurality of legs. The over-cannula has an outer diameter approximately less than or equal to an outer diameter of the outer layer. The at least one void includes a plurality of discrete voids spaced along a length of the wire. The plurality of legs join at a distal end of the retrieval assembly at a position separated from the void. The retrieval assembly is formed from a flat sheet. The flat sheet includes a first layer of a first material to form the outer layer and a second layer of a second material to form the inner core. The first layer has a varying cross-section. The wire has a substantially circular cross-section. The wire has a substantially hemispherical cross-section. The wire has a substantially triangular cross-section. The wire has a substantially tear-drop shaped cross-section.

In accordance with another aspect of the present disclosure, a medical retrieval device includes a cannula defining a lumen extending therethrough, the cannula having a first portion defining a first section of the lumen and a second portion distal to the first portion and defining a second section of the lumen, the second section of the lumen having a diameter less than a diameter of the first section of the lumen, and an expandable retrieval assembly including a plurality of legs, the retrieval assembly being connected to the cannula.

Embodiments of the medical device may include one or more of the following features. The lumen is configured to accept a medical device therethrough. The diameter of the second section of the lumen limits movement of the medical device. The second portion of the cannula includes a ring. The cannula includes a transition region between the first and second portions, the transition region having an inner diameter that tapers from the diameter of the first section of the lumen to the diameter of the second section of the lumen. The first portion and the second portion are distinct pieces of material connected to the transition region. The second portion includes the expandable retrieval assembly. The plurality of legs are formed from selective removal of material from the cannula. The device also includes a handle configured to receive a medical device therein, the handle including a handle stop configured to prohibit the advancement of the medical device through the lumen.

In accordance with still another aspect of the present disclosure, a medical retrieval system includes a retrieval device defining a lumen and having a first stop, and a medical device including a second stop, the lumen of the retrieval device being configured to accept the medical device therethrough, and the first and second stops being configured to prohibit advancement of the medical device beyond a desired distance.

Embodiments of the medical device may include one or more of the following features. The medical device is configured to reduce a size of a stone. The device is a laser fiber. The second stop is a cladding of the medical device. The second stop is a portion protruding from an outer surface of the medical device. The first stop is a first portion of the retrieval device having an inner diameter less than an inner diameter of a second portion of the retrieval device, the first portion of the retrieval device being distal to the second portion of the retrieval device. The first and second stops are at distal ends of the retrieval device and the medical device respectively. The first and second stops are at proximal ends of the retrieval device and the medical device respectively. The first stop includes a portion protruding from an inner surface of the retrieval device. The portion protruding is a ring.

In accordance with yet another aspect of the present disclosure, a medical retrieval device includes a sheath defining a first lumen, a retrieval assembly that is moveable relative to the sheath to achieve a collapsed position of the retrieval assembly within the first lumen and an expanded position of the retrieval assembly when extended outside the first lumen, the retrieval assembly connected to an elongate member positioned in the first lumen of the sheath and moveable relative to the sheath, a handle connected to a proximal end of the sheath and a proximal end of the elongate member, and a handle cannula extending within the handle and defining a second lumen having the elongate member therein, at least a portion of the handle cannula extending within the first lumen of the sheath, the handle cannula having a distal portion that is more flexible that a proximal portion of the handle cannula.

Embodiments of the medical device may include one or more of the following features. The handle causes relative movement between the elongate member and the sheath. The distal portion of the handle cannula extends within the first lumen of the sheath. The proximal portion of the handle cannula extends within the handle. At least a portion of the handle cannula of the device is selectively removed. The at least a portion of the handle cannula removed is an outer portion of the handle cannula. The distal portion of the handle cannula includes discrete segments. The handle cannula is made of composite wire.

In accordance with a further aspect of the present disclosure, a medical retrieval device includes an elongate member having an inner layer and an outer layer, the inner layer comprised of a first material and the outer layer comprised of a second material that is different than the first material and a retrieval assembly connected to a distal end of the elongate member.

Embodiments of the medical device may include one or more of the following features. The retrieval assembly includes a plurality of legs. The inner layer is nitinol and the outer layer is stainless steel. The inner layer defines a lumen. A proximal portion of the lumen of the device has an inner diameter larger than an inner diameter of a distal portion of the lumen. The elongate member further includes a stop positioned to prohibit the advancement of a, medical device beyond a desired distance from a tip of the retrieval assembly. At least a portion of the outer layer of the device is selectively removed. The selectively removed portion defines discrete sections. At least one of the first material or the second material is radiopaque. The retrieval assembly includes a basket having a plurality of legs. At least one of the legs has an inner layer and an outer layer, the inner layer being a different material than the outer layer. At least a portion of the outer layer of the at least one of the legs is selectively removed. The inner layer of the at least one of the legs is nitinol and the outer layer of the at least one of the legs is stainless steel.

Both the foregoing general description and the following detailed description are exemplary and explanatory only, and are not restrictive of the invention as claimed.

BRIEF DESCRIPTION OF THE DRAWINGS

FIG. 1b is a cross-sectional view of a portion of the proximal portion of FIG. 1a.

DETAILED DESCRIPTION

Exemplary embodiments of the present disclosure are illustrated in the accompanying drawings. Wherever possible, the same reference numbers will be used throughout the drawings to refer to the same or like parts.

Figure 1:
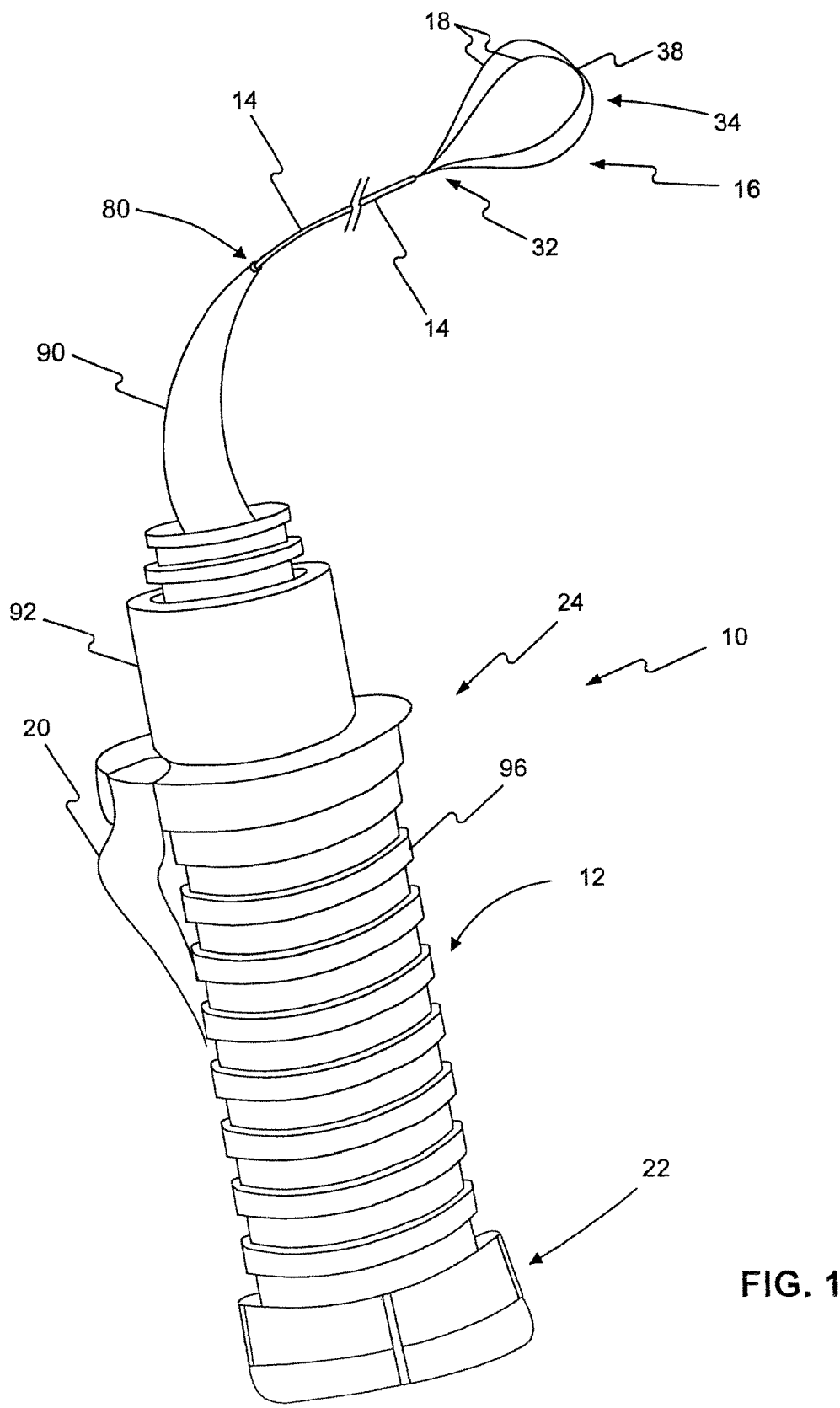
FIG. 1 is a medical retrieval device according to an embodiment of the present disclosure.

FIG. 1 illustrates a medical retrieval device 10 according to an embodiment of the present disclosure. Aspects of the device 10 may be used to assist in retrieving, for example, a stone from within the urinary tract of a patient. The stone may be a kidney stone, a struvite, a uric acid stone, a cystine stone, or other solid deposit commonly removed from a body structure or passageway within the body. Such stones may contain various combinations of chemicals including, but not limited to, calcium, oxalate, and phosphate. The stone may be of any size, and could have a length or diameter of approximately 1 mm to 12 mm. It is understood that these lengths and diameters are merely exemplary and that aspects of the present disclosure may assist in the removal of stones or other bodily tissue or foreign objects larger or smaller than those discussed herein. Stones may be of any shape and could be, for example, flat, round, smooth, or jagged. The device 10 may assist in the immobilization and removal of stones that are both impacted and free floating.

The retrieval device 10 may be advanced to a treatment site within the body through an access sheath, stent, or other access or dilatation device known in the art. In addition, the device 10 may be used in conjunction with an endoscope (not shown), or other type of intracorporeal scope known in the art. The endoscope may advance through the body over a guidewire to the treatment site. Alternatively, the endoscope may be independently fed to the treatment site without the use of a guidewire. Once the treatment site has been reached, the device 10 may be fed through an access port of the endoscope to gain access to the stone.

Depending on the location of the stone, it may be difficult for the user to reach the stone without causing trauma to the surrounding body tissue. For example, in some situations, the stone may be located in a calyx of the patient's kidney. In such situations, it may be difficult to retrieve the stone without damaging the kidney tissue surrounding the stone. It may also be difficult to expand parts of the device 10 in such a constricted area of the anatomy. Aspects of the device 10 may improve the user's ability to retrieve such stones.

Aspects of the device 10 may also assist in immobilizing a stone during stone reduction processes. For example, part of the device 10 may be positioned distal the stone so as to provide a backstop and prevent particles of the stone from migrating or escaping from the treatment site during or after a laser fiber or other device acts to break up the stone. During such a procedure, a laser fiber may be fed to the stone through a passage of the device 10. Alternatively, the laser fiber may be fed through an access port of an endoscope, external to the device 10, while the device 10 is disposed within the same or a different access port of the endoscope. The laser fiber may be activated and otherwise controlled by the user while it is within the body of the patient. The device 10 may also act as a sweeping device to sweep out of the body, stones and stone particles obtained from a reduction process.

As shown in FIG. 1, the device 10 may include a handle 12, a sheath 14, and a retrieval assembly. The retrieval assembly may be, for example, a basket 16 having a number of legs 18. The legs 18 may be separate wires that are joined together to form the basket 16. As will be described in greater detail below, the basket 16 may be opened and/or closed by moving the sheath 14 relative to the legs 18. Thus, a stone may be captured within the open basket 16 and retrieved by removing the device 10 from the body of the patient.

The sheath 14 may be formed from, for example, a rod, tube, cannula, stent, or other cylindrical structures, and may be substantially hollow. The sheath 14 may also be made from a flat sheet of material formed into a cylindrical shape. Other suitable structures and manufacturing methods may be used for sheath 14. The sheath 14 may be shaped to facilitate entry into and out of, for example, an endoscope (not shown) or other intracorporeal scoping device known in the art.

The sheath 14 may be formed from any suitable biocompatible material known in the art. Such materials may include, but are not limited to, stainless steel alloys (such as 300 and 400 series), cobalt chromium, nickel, titanium, nitinol, thermoforming plastic, polytetrafluoroethylene ("PTFE"), and expanded polytetrafluoroethylene ("EPTFE"). The sheath 14 may also be a metal coated with a polymer.

The overall length and diameter of the sheath 14 may vary depending on the application. For example, a relatively long sheath 14 may be advantageous for retrieving stones or other calculi deep within the body of the patient. In addition, a sheath 14 having a relatively small diameter may be advantageous for retrieving stones from restricted passageways within the human urinary tract. The sheath 14 may include an open lumen or channel 78 (shown in FIG. 1b) and may be sized to pass over the legs 18 of the basket 16, thereby collapsing the basket 16. The sheath 14 may also be sized to be easily withdrawn, thus allowing the basket 16 to expand. As will be described in greater detail below, the sheath 14 may be operatively connected to a slide 20 of the handle 12 by way of a connector 92. Through this connection, the user may manipulate the sheath 14 relative to the basket by actuating the slide 20.

The legs 18 of the basket 16 may be formed by, for example, laser cutting, chemical etching, die cutting, grinding, or mechanically slicing a single piece of material. As a result, the width of the cuts may define the width and mechanical behavior of each of the basket legs 18, and the desired width may vary depending on the particular application. For example, it may be advantageous to have relatively narrow basket legs 18 when retrieving a relatively large stone from within the body. Alternatively, the legs 18 may be formed by, for example, welding, soldering, tying, or otherwise connecting separate pieces of wire or other material together. Although FIG. 1 shows four legs, it is understood that the basket 16 may include any number of legs depending on the desired characteristics and stone retrieval capabilities of the resulting basket 16.

Figure 1A:
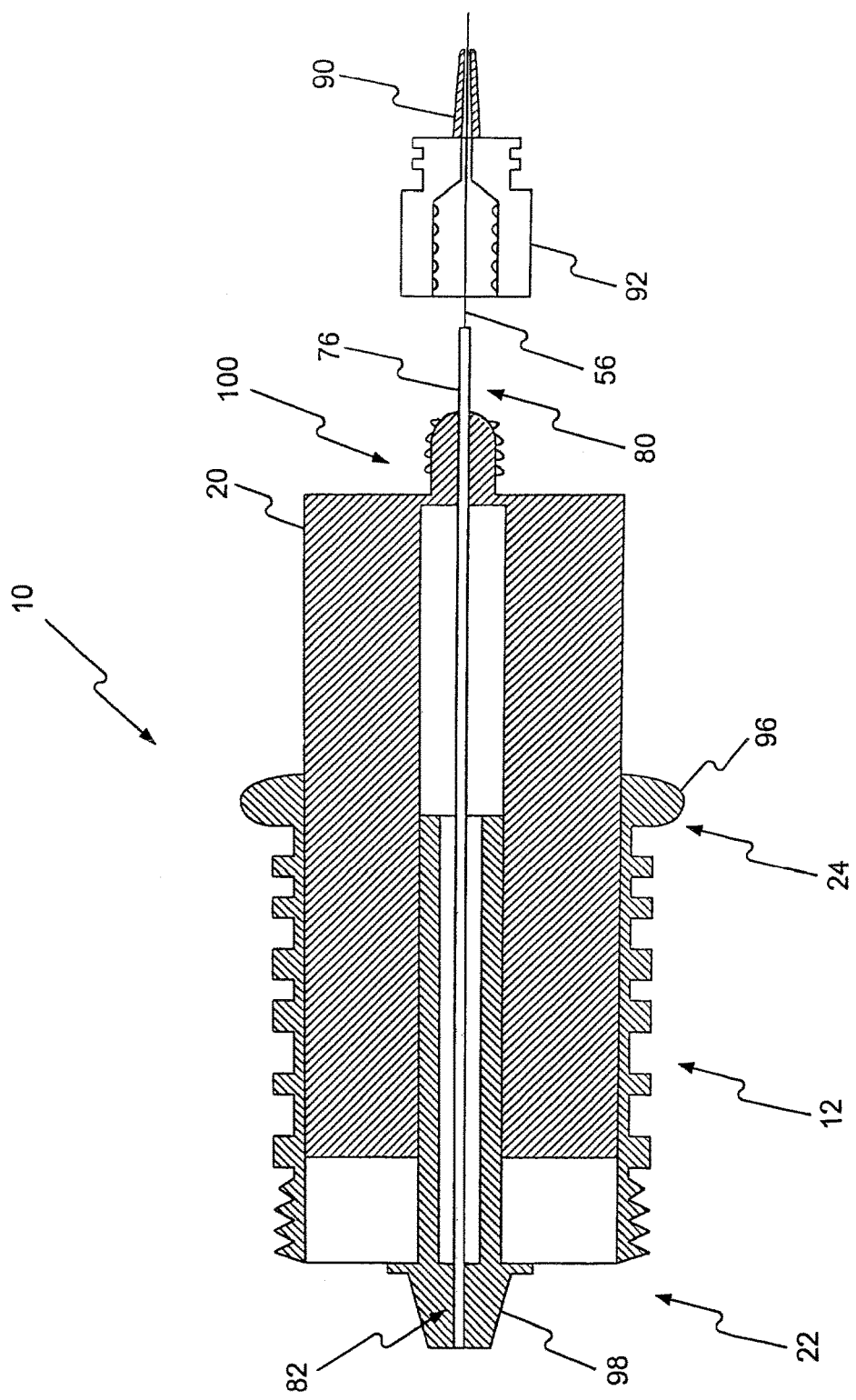
FIG. 1a is an exploded cross-sectional view of a proximal portion of the medical retrieval device of FIG. 1.

An end of each leg 18 may be connected to an elongate member or cannula 56 (see, e.g., FIG. 9), at least a portion of which may be disposed within the sheath 14. The cannula 56 may extend through the entire length of the sheath 14 and, as shown in FIG. 1a, the cannula 56 may be fixedly connected to a handle cannula 76. At least a portion of the cannula 56 may extend into a lumen of the handle cannula 76 and in some embodiments, the cannula 56 may extend through the entire length of the handle cannula 76. The cannula 56 may be connected to the handle cannula 76 by any conventional means such as, for example, crimping, pinching, adhering, heat sealing, or a combination thereof. For example, in one embodiment of the present disclosure, the cannula 56 may extend through the entire length of the handle cannula 76 and may be glued thereto at a distal portion 80 of the handle cannula 76, crimped at a middle portion, and pinched at a proximal portion 82.

At least a portion of the handle cannula 76 may be disposed within the handle 12. As shown in FIG. 1a, the handle 12 may include a housing 96, a sleeve 98, and a slide 20. The sleeve 98 may be fixed relative to the housing 96, and the handle cannula 76 may be fixedly connected to the sleeve 98 by any conventional means such as, for example, crimping, pinching, adhering, heat sealing, or a combination thereof. For example, the proximal portion 82 of the handle cannula 76 may be pinched by the sleeve 98 at the proximal end 22 of the handle 12. This pinching may be facilitated by, for example, a threaded cap (not shown) or other like means attached to the proximal end 22 of the handle 12. As a result, the handle cannula 76 and at least a portion of the cannula 56 may be fixed with respect to the handle housing 96.

The slide 20, on the other hand, may be moveable relative to the handle housing 96 and may be actuated by the user to expand and collapse the basket 16. FIG. 1 shows slide 20 in a retracted position, in which basket 16 is in an expanded state. FIG. 1a shows slide 20 in an extended position, such that basket 16 achieves a collapsed state within sheath 14.

In some embodiments, a connector 92 may be attached to the distal portion 100 of the slide 20. The connector 92 may be any type of connector known in the art and may be attached to the slide 20 by any conventional means such as, for example, threads, adhesives, heat shrinks, or a combination thereof. Thus, when the slide 20 is actuated, the connector 92 may move in concert with the slide 20 relative to the housing 96, sleeve 98, handle cannula 76, and cannula 56.

Figure 1B:
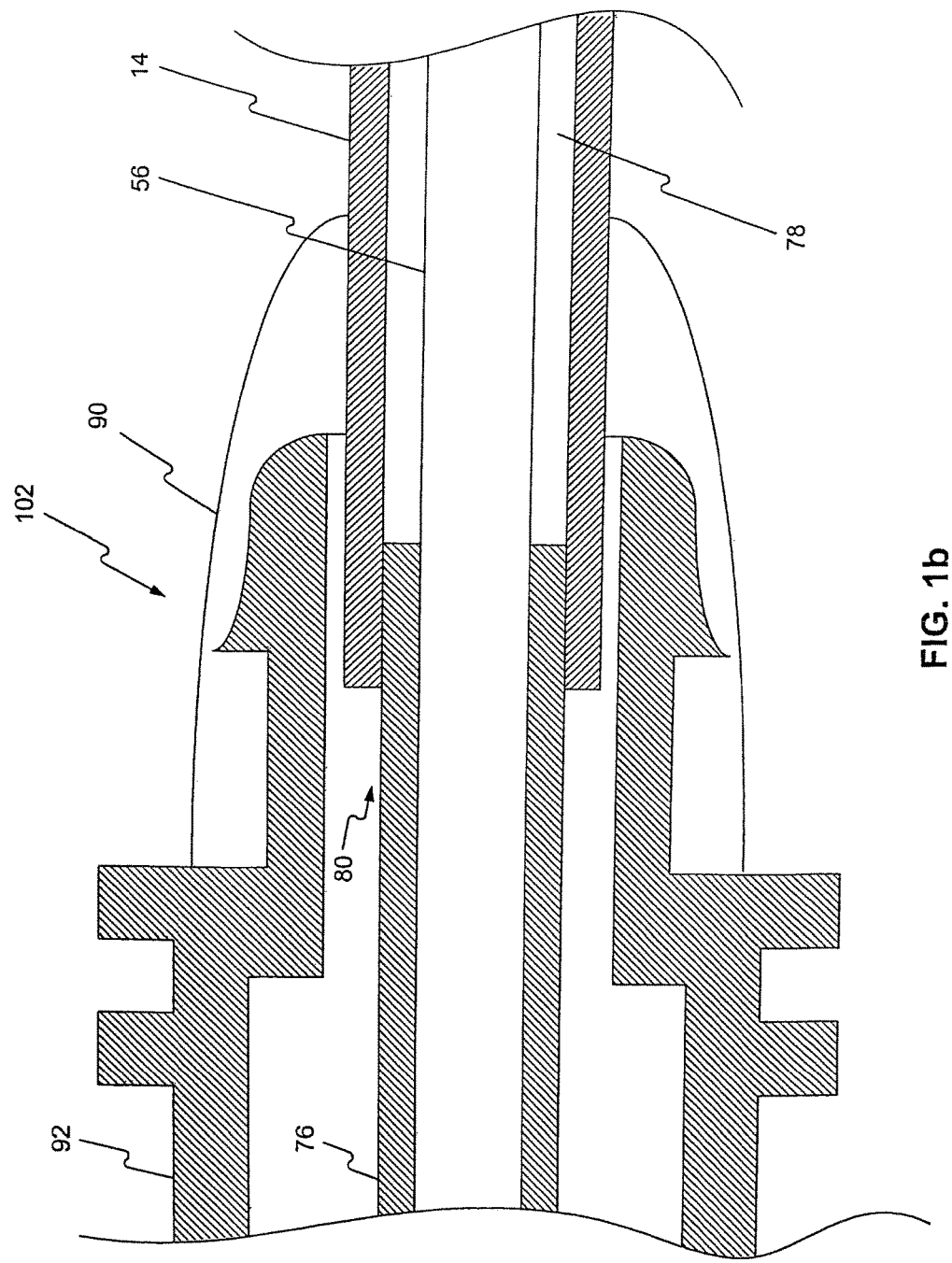

As shown in FIG. 1b, the connector 92 may facilitate connection between, and joint movement of, the slide 20 and the sheath 14. The sheath 14 may be rigidly connected to the connector 92 by any conventional means such as, for example, adhesives, crimping, threading, heat shrinking, or a combination thereof. In one exemplary embodiment of the present disclosure, at least a portion of the sheath 14 may be disposed within the connector 92. A layer of melt liner or other adhesive known in the art may be applied to the connector 92 and/or the sheath 14, and a strain relief 90 may be heat sealed to portions of both the connector 92 and the sheath 14. The melt liner and the strain relief 90 may form a rigid bond between the connector 92 and at least a portion of the sheath 14, thereby facilitating a connection between the sheath 14 and the slide 20.

Actuating the slide 20 in a proximal direction (such as to the position shown in FIG. 1) may withdraw the sheath 14 relative to cannula 56 and handle cannula 76, and may allow the basket 16 to at least partially open. As used herein, the term "proximal" refers to a direction, location, or position closest to the operator. In some embodiments, while the basket 16 is in the open position, the handle cannula 76 may extend into the open lumen or channel 78 of the sheath 14 approximately 1 to 2 inches, and more particularly, about 1.33 in. The flexibility or rigidity of a strain relief section 102 of the device 10 may vary based on a number of factors such as, for example, the distance the handle cannula 76 extends into the sheath 14.

Actuating the slide 20 in a distal direction may extend at least part of the sheath 14 over at least part of the legs 18 and may at least partially collapse the basket 16. As used herein, the term "distal" refers to a direction, location, or position furthest from the operator. While the basket 16 is in the closed position, the handle cannula 76 may extend only slightly into the open lumen or channel 78 of the sheath 14, for example, only approximately 0.014 inches.

In some embodiments of the present disclosure, portions of a medical retrieval device may be comprised of material, composite material, or structure, that imparts desired characteristics to that portion. The desired characteristics imparted to that portion may include, for example, increased flexibility, increased stiffness or rigidity, increased texture, and/or varying geometry to improve the functionality of that portion and/or improve radiopacity to enhance imaging and viewing. For example, the retrieval device basket may have one or more legs composed of a composite wire to balance the need for both basket strength and basket flexibility. In other embodiments, the device may include one or more cannulas having materials or structure to achieve desired characteristics. These and other embodiments are described below.

Aspects of the device 10 may utilize composite wire or tubing. As used herein, the term "composite" refers to the wire or tube being comprised of more than one material. A composite wire or tube may include, for example, at least two distinct layers of different material. The distinct layers may be co-axial. Alternatively, the composite wire or tube may include more than one material mixed, blended, extruded, or otherwise combined together to form a wire or tube having a substantially uniform cross-section. Thus, instead of forming distinct layers of material, the ratio of each different material may be substantially constant across the entire cross-section of the composite wire. As a further alternative, the more than one material may be combined together across the cross-section in varying amounts.

The composite wire or tube may be made of, for example, alloys of nitinol, stainless steel, titanium, cobalt chromium, gold, tantalum, platinum, polymers, and/or any other suitable materials known in the art. The composite wire or tube may also be made of numerous types of thermoplastic polymers and flouropolymers such as, for example, PTFE, EPTFE, ethylene vinyl acetate ("EVA"), polyethylene, polypropylene, or other suitable materials. Any of the above materials, and others, may be used interchangeably to form a core and/or an outer sleeve of the composite wire or tube. In addition, at least one of the materials used in the composite may be radiopaque. Such materials may enable the user to view aspects of the device 10 under fluoroscopic examination.

The ratio of one material to another may vary along at least a portion of the composite wire or tube to impart, for example, elasticity, shape memory, strength, flexibility, rigidity, radiopacity, varying texture, varying geometry, or other desired characteristics to the device 10. The composition of each different material used may also vary based on these desired characteristics. For example, the ratio of stainless steel to nitinol in a composite wire or tube of the device 10 may be selected based on the desired strength and/or flexibility of aspects of the device 10. The type of stainless steel alloy used may be 300 series, 400 series, or any other formulation of stainless steel known in the art depending on, for example, the desired strength of the composite. In addition, the relative proportion of nickel to titanium in, for example, the nitinol layer may also be selected based on the characteristics mentioned above and/or other desired characteristics.

The composite wire or tube of embodiments of the present disclosure may be formed by, for example, co-extrusion, drawing, lamination, heat shrinking, or any other process known in the art. In one embodiment, PTFE may be heat shunk over, for example, a nitinol core. In another embodiment, a core may be placed inside of, for example, a stainless steel sleeve which may then be coated with tetrafluoroethylene ("TFE"). In still another embodiment, the different materials used may be rolled or brazed to form a flat composite sheet of multi-metallic or multi-polymer material. The sheet may then be, for example, ground, laser cut, or chemically etched to form the composite wire or tube of embodiments of the present disclosure.

The shape and size of the composite wire or tube may also be manipulated to impart desired characteristics to the composite wire or tube, thereby enhancing the functionality of certain aspects of the device 10.

Figure 2:
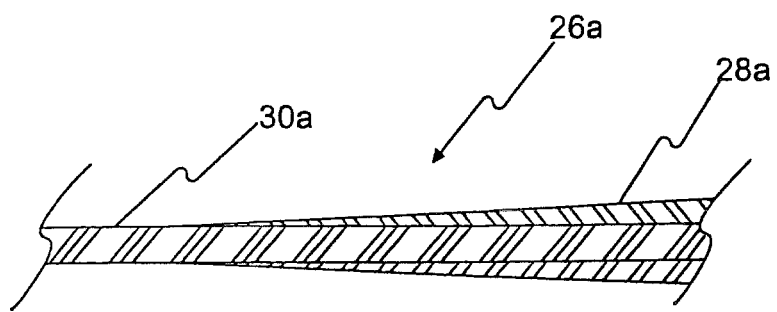
FIG. 2 is a plan cross-sectional view of a length of composite wire according to an embodiment of the present disclosure.

FIGS. 2-8 show various embodiments of composite wires or tubes 26. As shown in FIG. 2, an outer sleeve 28a of the composite wire 26a may taper down to a core 30a to add variable flexibility to the composite wire 26a. Alternatively, the outer sleeve 28a may have, for example, a constant thickness along at least a portion of the core 30a, and aspects of the device 10 may have constant mechanical characteristics along that portion. In addition, sleeve 28a and core 30a may be comprised of different materials. The outer sleeve 28a may range in size from approximately 25.5 gage wire to approximately 28 gage wire. The core 30a may have a diameter in the range of approximately 0.004 mm to approximately 10 mm. Other sizes, depending on the desired application, may be used.

Figure 3:
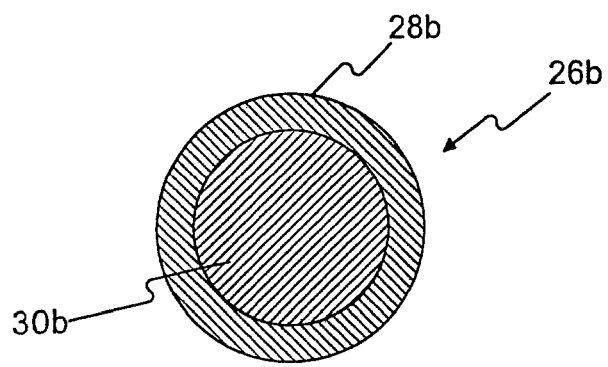
FIG. 3 is an end cross-sectional view of a composite wire according to an embodiment of the present disclosure.
Figure 4:
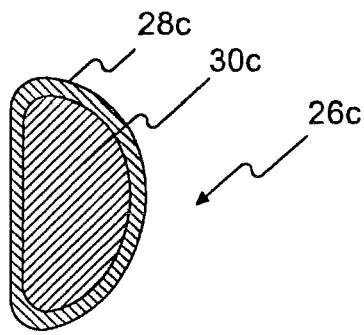
FIG. 4 is an end cross-sectional view of a composite wire according to another embodiment of the present disclosure.
Figure 5:
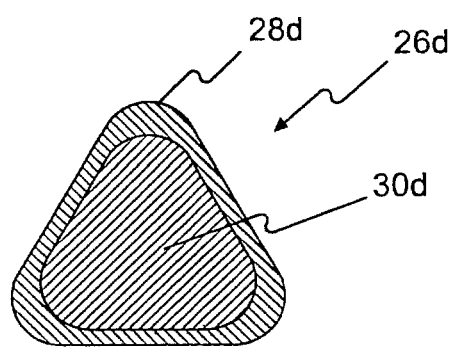
FIG. 5 is an end cross-sectional view of a composite wire according to yet another embodiment of the present disclosure.
Figure 6:
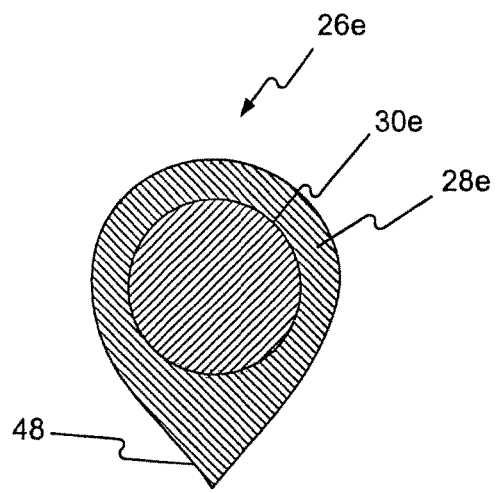
FIG. 6 is an end cross-sectional view of a composite wire according to still another embodiment of the present disclosure.

As another example, and as shown in FIG. 3, the composite wire 26b may include a core 30b having a substantially circular cross-section and a substantially cylindrical outer sleeve 28b. The composite wire 26c alternatively may have a D-shaped (or hemispherical) cross-section as shown in FIG. 4, a substantially triangular-shaped cross-section as illustrated by wire 26d of FIG. 5, or a substantially tear-drop shaped cross-section as shown by wire 26e in FIG. 6. The composite wire 26 may be pressed or otherwise formed into the desired shape and may have a relatively sharp edge 48 on at least one surface (FIG. 6). The edge 48 may facilitate, for example, fracturing, slicing, or otherwise reducing the size of a stone.

Figure 7:
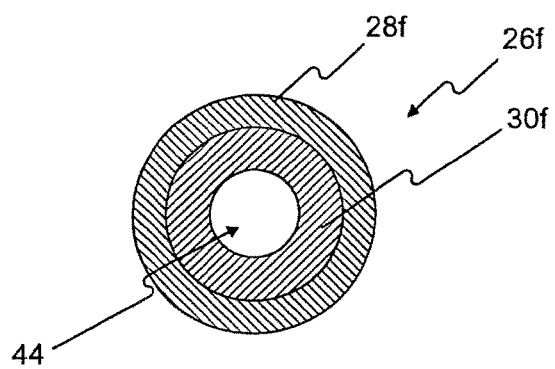
FIG. 7 is an end cross-sectional view of a composite wire according to a further embodiment of the present disclosure.

FIG. 7 shows a composite tube 26f with a center passage 44. In such an embodiment, the core 30f may be substantially hollow. The center passage 44 may be sized to allow, for example, a laser fiber (not shown) or other device known in the art to pass through the core 30f to a treatment site. The treatment site may correspond to the location of, for example, a stone within the urinary tract of a patient.

In some embodiments of the present disclosure, the cross-sectional area or other characteristics of the core 30 may be any size or dimension relative to the outer sleeve 28 of the composite wire or tube 26. For example, although FIG. 4 illustrates a core 30c having larger cross-sectional area than that of the outer sleeve 28c, in other embodiments of the present disclosure the outer sleeve 28 may have a larger cross-sectional area than that of the core 30.

Figure 8:
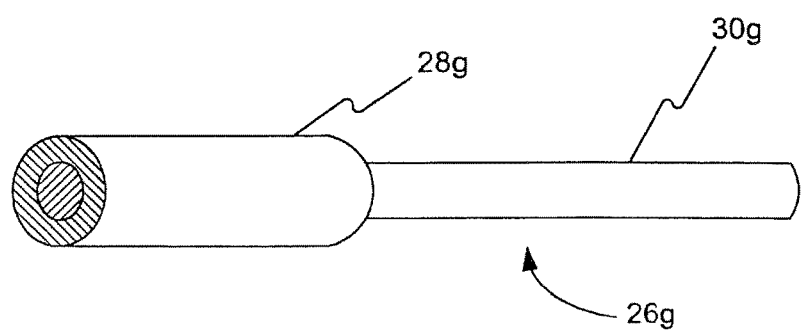
FIG. 8 is a perspective view of a composite wire according to an embodiment of the present disclosure.

In various embodiments, at least a portion of a composite wire or tube may be removed to define one or more voids in the wire or tube to alter certain characteristics of the wire or tube. For example, FIG. 8 illustrates an embodiment of the present disclosure in which at least a portion of the composite wire 26g may be ground, chemically etched, or otherwise removed. The portion removed may be at least a portion of the outer sleeve 28g. In areas where the outer sleeve 28g has been removed to expose core 30g, at least a portion of the core 30g may be removed as well. Removing at least a portion of the composite wire 26g may increase the elasticity, decrease the stiffness, and/or improve the ability of the composite wire 26 to grasp a stone and/or limit the stone's movement. For example, the composite wire 26g illustrated in FIG. 8 may have a nitinol core 30g and a stainless steel outer sleeve 28g. The stainless steel may add strength and stiffness to a composite wire 26 while the nitinol may add elasticity, shape memory, and flexibility. Thus, removing at least a portion of a stainless steel outer sleeve 28 may reduce the strength and/or stiffness of the parts of the device 10 utilizing the composite wire 26, and may increase the elasticity, flexibility, shape memory, and/or gripping capabilities of those parts.

Figure 9:
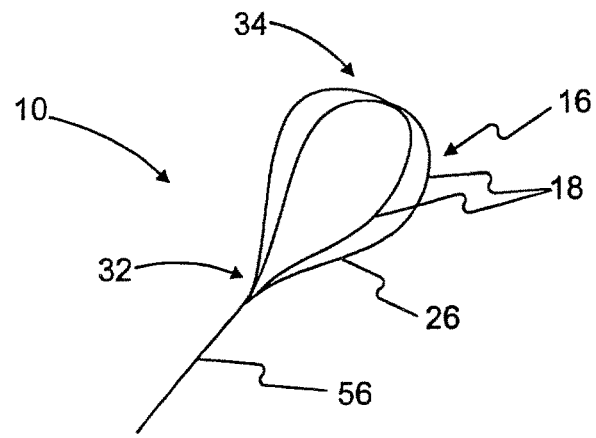
FIG. 9 is a basket according to an embodiment of the present disclosure.

Selectively removing portions of the composite wire 26 may also assist in welding, bonding, or otherwise connecting various parts of the device 10. For example, as shown in FIG. 9, the composite wire 26 may form legs 18 in a basket 16 of the device 10. In this embodiment, the ground or etched portions may assist in joining the wires 26 at the proximal end 32 and/or the distal end 34 of the basket 16. This may be accomplished in any number of ways.

Figure 10:
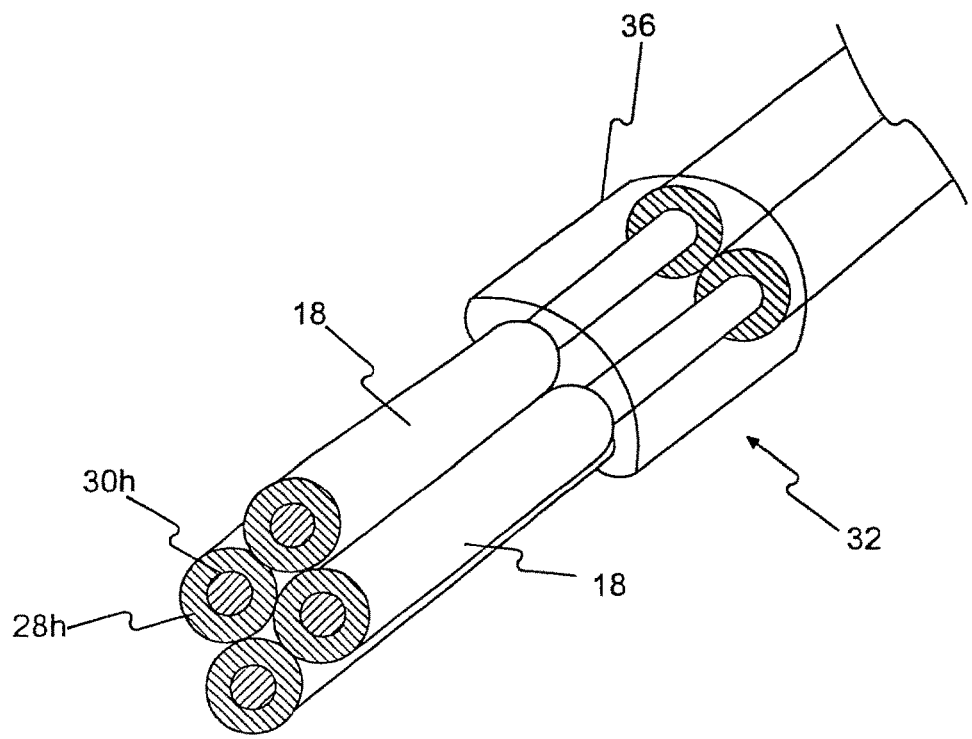
FIG. 10 is the proximal end of a basket according to an embodiment of the present disclosure.

For example, as FIG. 10 illustrates, the proximal end 32 of the basket 16 may be formed by connecting each of the legs 18 with an over-cannula 36. The over-cannula 36 may be made of any material known in the art and may be crimped, swaged, heat shrunk, welded, or otherwise attached to the legs 18 so as to bind the legs 18 together. The ground or etched portions of the composite wire 26 may allow for a reduced diameter at the proximal end 32 in a location corresponding to the over-cannula 36. The reduced diameter may create a low profile joint at the location, and may allow for the use of larger diameter legs 18 while reducing, for example, the diameter of the sheath 14 (not shown) required.

Figure 11:
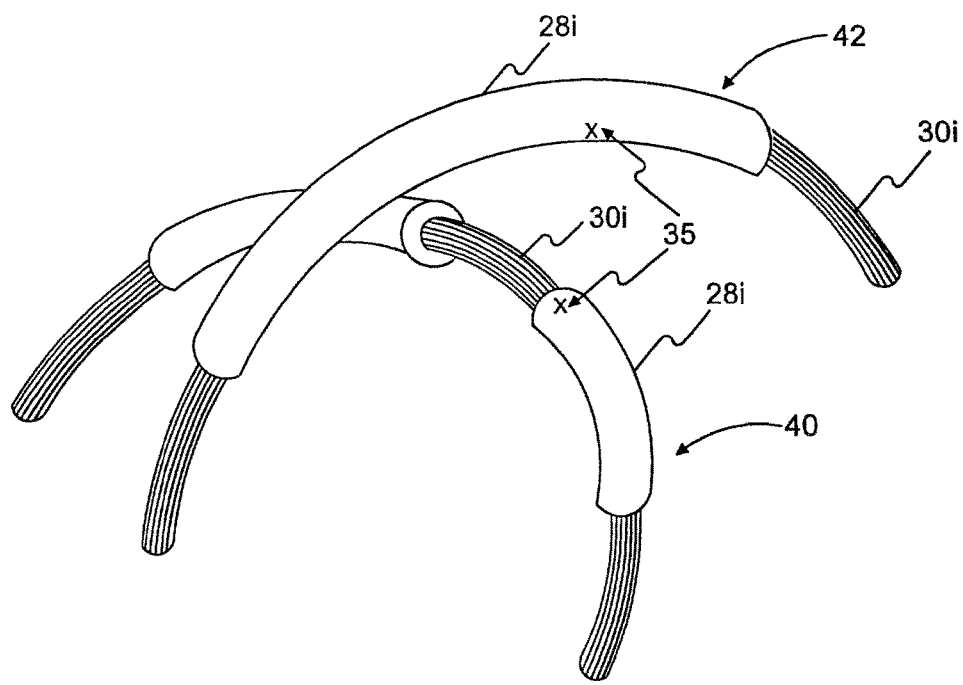
FIG. 11 is an unformed joint between two composite wires, according to an embodiment of the present disclosure.

As a further example, FIG. 11 illustrates an embodiment of the present disclosure in which a portion of a first composite wire leg 40 has been removed to expose the core 30i. In this embodiment, the removed portion may allow for a low profile weldable joint at a tip of the basket 16. In such a joint, at least a portion of the outer sleeve 28i of the first leg 40 may be bonded to at least a portion of the outer sleeve 28i of an adjacent second leg 42 of the basket 16. This bond or weld may be made at, for example, positions 35. The tip may be substantially smooth and may minimize any damage caused to kidney tissue while retrieving a stone. In this embodiment, the outer sleeves 28i may be made of materials such as, for example, stainless steel or other materials capable of being welded or otherwise bonded together, and the core 30i may be comprised of, for example, nitinol. This joint may be rigid relative to the rest of the basket 16 and may provide a strong opening or dilation force when the sheath 14 is withdrawn and the basket 16 is allowed to expand. A strong dilation or opening force may be required in applications where the basket 16 is opened in constricted areas within, for example, the urinary tract of a patient.

Moreover, combining the characteristics of the rigid joint illustrated in FIG. 11 with the ground or selectively etched legs 18 described above may improve the overall flexibility of the basket 16 while maintaining a strong opening force. Alternatively, a relatively flexible joint may be combined with legs 18 having little or no grinding or etching. The resulting basket 16 may be relatively strong and less flexible while being relatively easily collapsible. A basket 16 with such characteristics may be collapsed more easily as the sheath 14 is extended.

Figure 12:
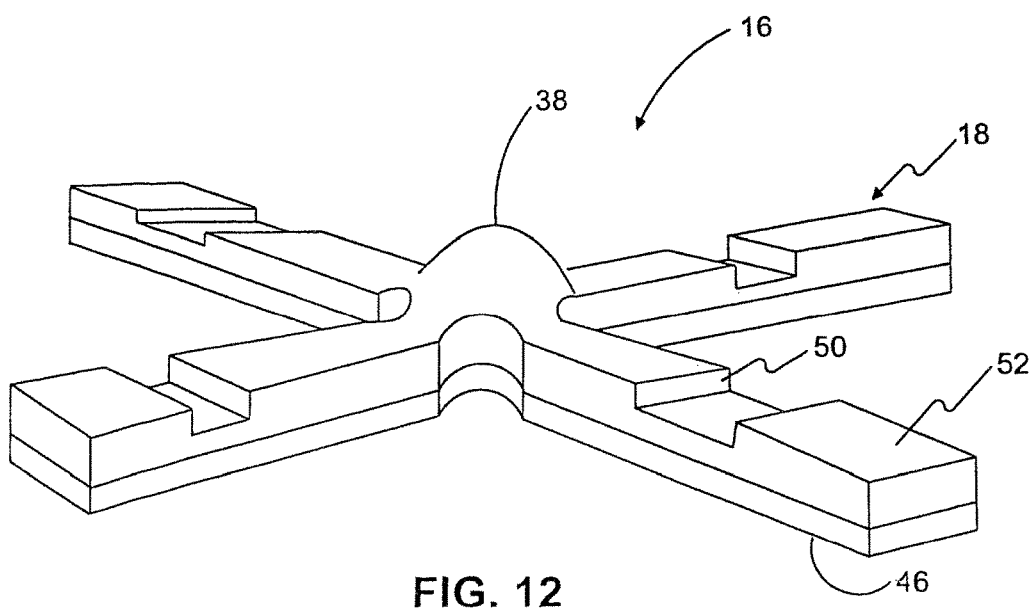
FIG. 12 is an unformed basket according to an embodiment of the present disclosure.

FIG. 12 illustrates a further embodiment of the present disclosure in which a basket 16 of the device 10 may be selectively ground or etched from a flat sheet 52 of material. The material may be, for example, 304 or 455c stainless steel. In some embodiments, the sheet 52 may also include a layer 46 of nitinol laminate or other laminates known in the art. As shown, the unformed basket 16 may include a selectively ground or etched tip 38 of a shape and size known in the art. The tip 38 may be, for example, rounded, dull, or otherwise shaped so as to minimize the trauma caused when manipulating the basket 16 within the body of a patient. The basket 16 may further include a number of selectively ground or etched features 50 on at least one of the legs 18. In such an embodiment, the outer sheet 52 may define at least one void that may expose the inner layer 46. The etched features 50 may be of any shape or size known in the art and may be on outer sheet 52 and/or inner layer 46 of the legs 18. The etched features 50 may selectively increase the flexibility of the legs 18 and may impart any of the other desired characteristics mentioned above to the resulting basket 16. The etched features 50 may also facilitate the formation of one or more low profile joints such as those described above. FIG. 12 shows basket 16 in an unfinished state. The ends of each leg opposite tip 38 would join to form a finished basket 16. The ends may be joined in any suitable manner, including those described herein.

Figure 13:
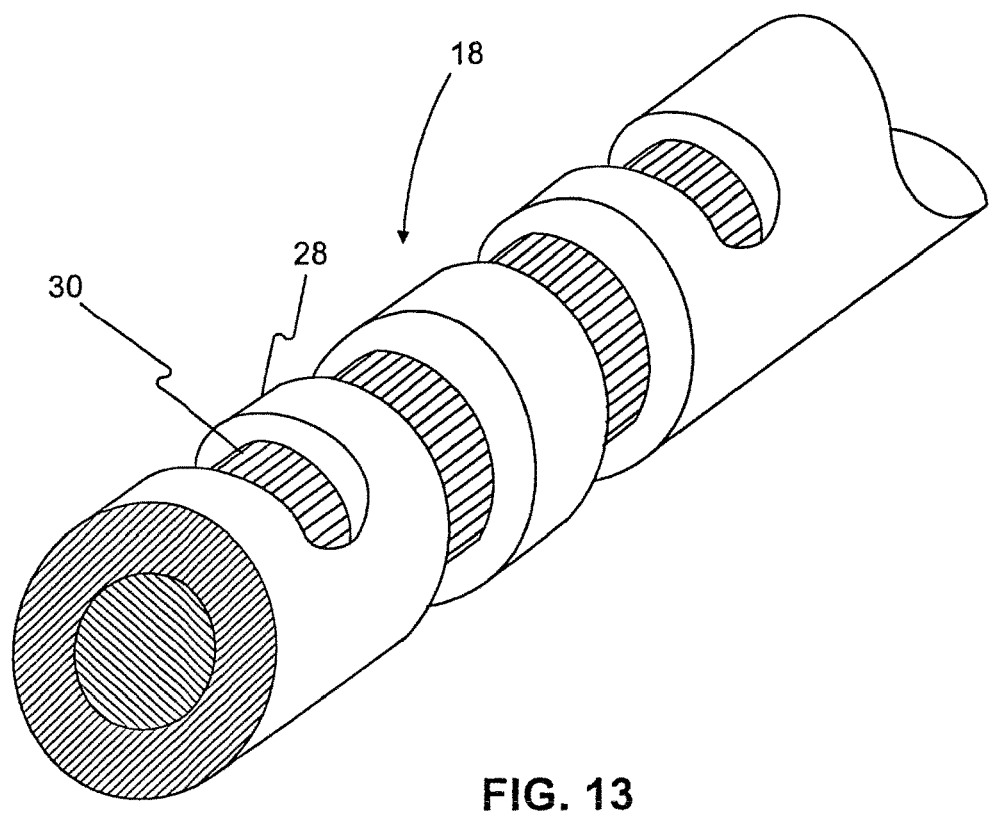
FIG. 13 is a basket leg according to an embodiment of the present disclosure.
Figure 14:
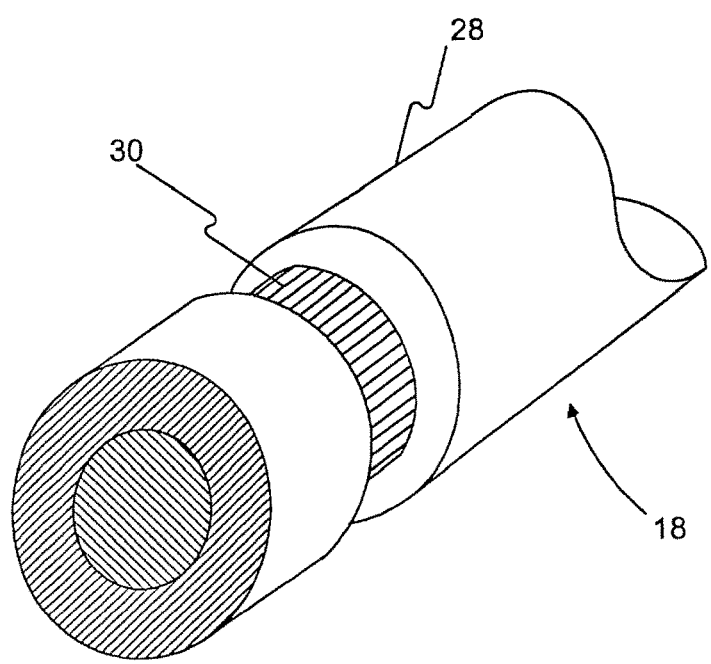
FIG. 14 is a basket leg according to another embodiment of the present disclosure.
Figure 15:
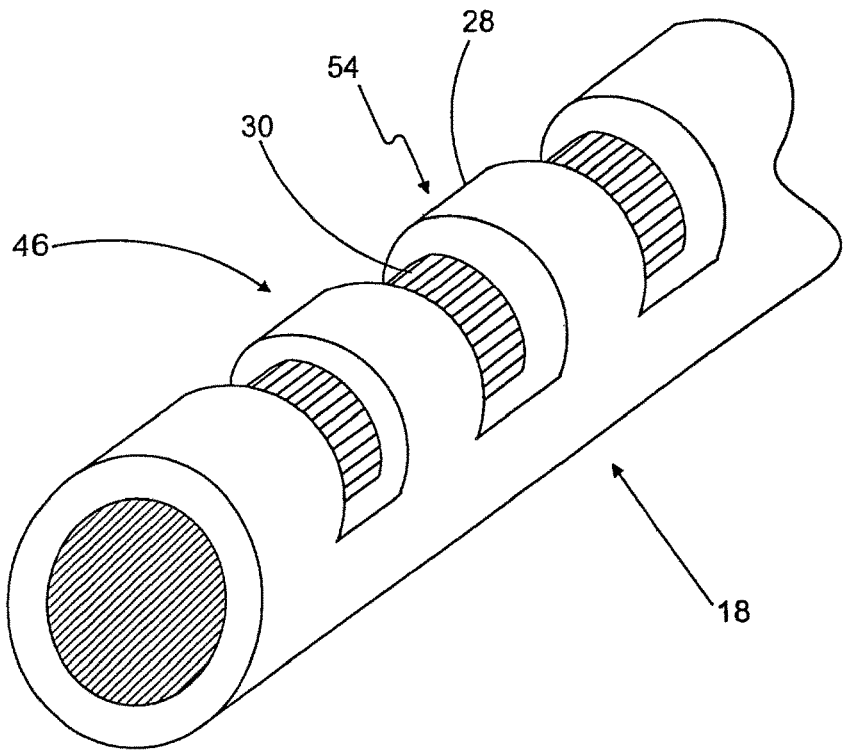
FIG. 15 is a basket leg according to still another embodiment of the present disclosure.

In some embodiments, the legs 18 of the present disclosure may be selectively ground or etched in any suitable configuration. These configurations may remove at least a portion of a relatively rigid outer sleeve 28 and/or may expose at least a portion of a relatively flexible core 30. In such an embodiment, the outer sleeve 28 may define at least one void. Thus, selectively grinding or etching one or more basket legs 18 may produce a basket 16 having a desired flexibility, shape memory, strength, and/or other characteristics. The legs 18 may be, for example, selectively ground or etched in a spiral configuration as shown in FIG. 13 or a circumferential groove configuration as shown in FIG. 14. FIG. 15 shows partial circumferential grooves selectively ground or etched at one side surface of leg 18. In doing so, the side surface may form an inner surface 46 of a leg 18 that has teeth to aid in gripping a stone. For example, a stone may be gripped between teeth 54 shown in FIG. 15. Selective grinding or etching may also produce spikes, treads, serrations, or other structures or textures that may provide at least some of the desired characteristics mentioned above. Such structures or textures may also improve the gripping capabilities of at least a portion of the inner surface 46 of the legs 18. In one embodiment, such structures or textures may provide multi-point contact with a stone and may be pointed away from sensitive tissue within the body of the patient so as not to cause trauma thereto.

Figure 16:
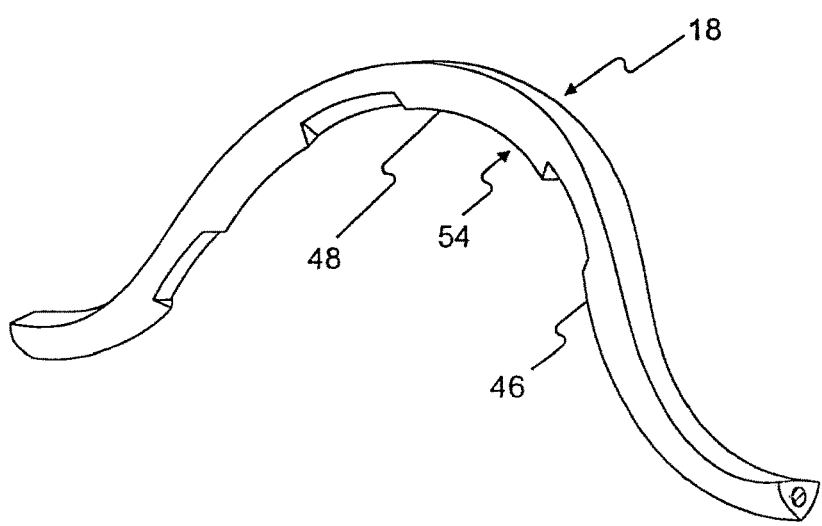
FIG. 16 is a basket leg according to yet another embodiment of the present disclosure.

FIG. 16 illustrates an additional embodiment of a selectively ground or etched basket leg 18 of the present disclosure. As shown, teeth 54 of leg 18 may be formed by removing at least a portion of the inner surface 46 of the leg 18. Although FIG. 16 illustrates an embodiment in which the teeth 54 are formed with a sharp edge 48 of a substantially triangular leg 18, it is understood that teeth 54 may be formed in composite wires 26 having, for example, any other cross-sectional shape referred to in this disclosure or any other shape known in the art. The teeth 54 may be of any size and/or shape necessary to produce the desired grasping, cutting, stone reduction, and/or other characteristics of the basket 16. The legs 18 may include any number of teeth 54 in any location to produce these desired characteristics.

Figure 17:
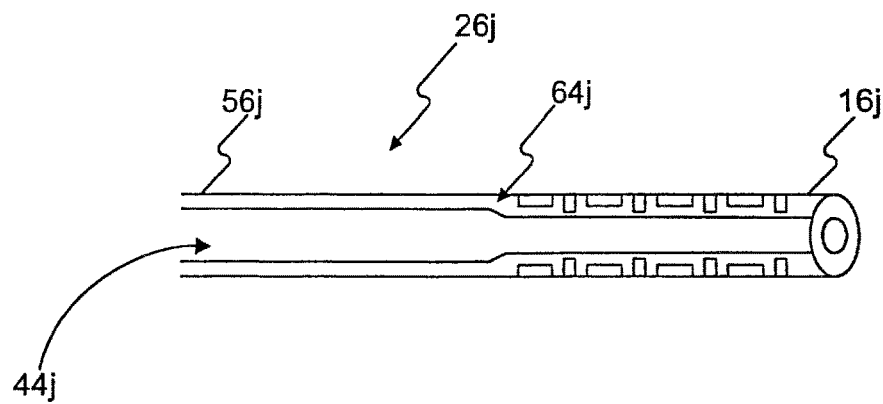
FIG. 17 is a cross-sectional view of a medical retrieval device according to an embodiment of the present disclosure.

As mentioned above, composite wires and/or tubes of the present disclosure may be used to form various aspects of the device 10. For example, as shown in FIG. 17, a composite tube 26j may form a hollow cannula 56j and a basket 16j. The basket 16j illustrated in FIG. 17 may be made out of the same piece of composite tube 26j as the cannula 56j or out of a different piece or pieces of material that are then joined together. The basket 16j may also have the same inner diameter as the cannula 56j or may have a different inner diameter.

For example, in one embodiment, the basket 16j may be laser cut or otherwise formed from a different piece of hollow composite tube 26j than the cannula 56j, and may have a larger wall thickness and a smaller inner diameter than the cannula 56j when in the collapsed position shown in FIG. 17. A basket 16j of such an embodiment may have a relatively strong opening force and relatively rigid legs 18 as compared to baskets having relatively larger inner diameters. In such an embodiment, the basket 16j may be connected to the cannula 56j through, for example, weldments, gluing, fusing, or other assembly processes known in the art. The composite tube 26j of the cannula 56j may be made of any of the materials mentioned above. In addition, the cannula 56j may be made from combinations of, for example, urethanes, nylons, pebax, braided plastic tubing, or other plastics. Depending on their proportion and location in the composite tube 26j of the cannula 56j, these materials may selectively increase or decrease the strength of cannula 56j and may assist in forming a tapered inner diameter of the cannula 56j.

In this embodiment, the basket 16j may be connected to the cannula 56j at a transition region 64j. Thus, the inner diameter of the device 10 may gradually or abruptly change from the larger inner diameter cannula 56j to the smaller inner diameter basket 16j at the transition region 64j. The transition region 64j may be a distal portion of cannula 56j or a proximal portion of basket 16j. Alternatively, one or more transition tubes (not shown) having, for example, progressively smaller inner diameters or tapered inner diameters may be part of the device 10 forming the transition region 64j between cannula 56j and basket 16j to facilitate a relatively smooth inner diameter transition.

As a further alternative, in the embodiment of the present disclosure in which the basket 16j is made from the same piece of material as the cannula 56j, the inner diameter may gradually or abruptly taper to form the transition region 64j of the single piece.

In any of the embodiments discussed above, the cannula 56 may provide a center passage 44 sized to allow, for example, a laser fiber or other desired medical device (not shown) to pass through the device 10. It may be desirable, however, to limit the distance that the laser fiber or other medical device may travel within the center passage 44 to, for example, avoid damaging the device 10. Thus, in some embodiments, the device 10 may include a laser fiber stop to prevent the tip of the laser fiber from advancing, for example, further than a pre-determined safe distance from the tip 38 or other portions of the basket 16. This predetermined distance may prevent the laser fiber from delivering enough laser energy to damage the tip 38 or other portions of the basket 16.

As will be described in greater detail below, in some embodiments, a distal portion of the laser fiber may have a smaller diameter than that of a proximal portion of the laser fiber. To accommodate such a laser fiber, the distal retrieval assembly of retrieval device 10 that may receive the distal portion of the fiber may have a smaller inner diameter than the inner diameter of the elongate cannula 56. In such a case, only the distal portion of the laser fiber may extend into basket 16. In such embodiments, and as shown in the embodiment of FIG. 17, each leg 18 of the basket 16 may have a relatively larger cross-sectional area and/or the basket 16 of the device 10 may have a stronger opening force, due to the decrease inner diameter of the distal retrieval assembly.

Figure 18:
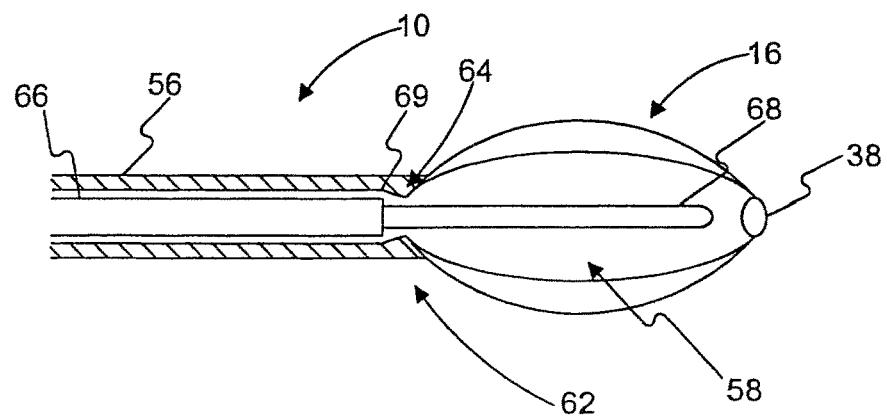
FIG. 18 is a cross-sectional view of a medical retrieval device according to another embodiment of the present disclosure.

A laser fiber stop of the present disclosure may take a variety of different forms. For example, as shown in FIG. 18, the transition region 64 may act as a laser fiber stop 69. The laser fiber 58 may include a larger diameter proximal section 66 that may include cladding, and a smaller diameter distal fiber section 68 that may be devoid of cladding. As the laser fiber 58 is advanced within the cannula 56 toward the distal end 62, the section 66 of the laser fiber 58 may contact the transition region 64 while the fiber section 68 may extend into at least a portion of the open basket 16. The transition region 64 may be sized to mechanically stop section 66 from advancing in the distal direction once this contact is made and, in doing so, may also prohibit further advancement of the fiber section 68.

Figure 19:
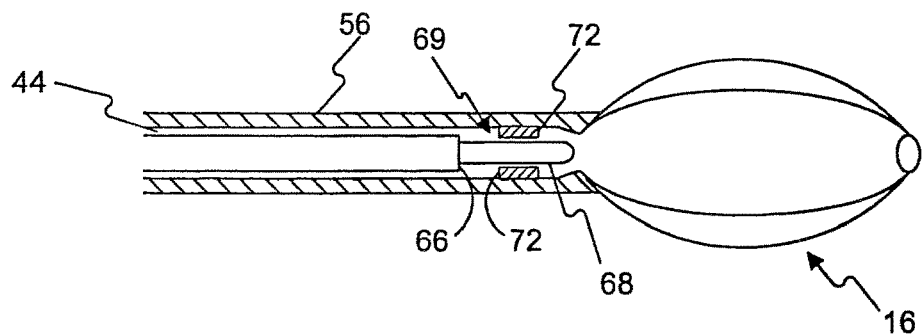
FIG. 19 is a cross-sectional view of a medical retrieval device according to still another embodiment of the present disclosure.

As shown in FIG. 19, in another embodiment, the laser fiber stop 69 may be a cannula stop 72 connected to the inner diameter of the cannula 56. The cannula stop 72 may be a single ring mounted to an interior surface of the cannula 56 and may be sized and dimensioned to allow the fiber section 68 to pass through a hole in the center of the ring while mechanically stopping larger diameter section 66. Alternatively, the cannula stop 72 may be one or more individual pieces of material mounted to the distal end of the cannula 56. The one or more pieces may be sized and positioned to prohibit the cladding 66 from advancing while allowing at least a portion of the fiber section 68 to pass into the basket 16.

Figure 20:
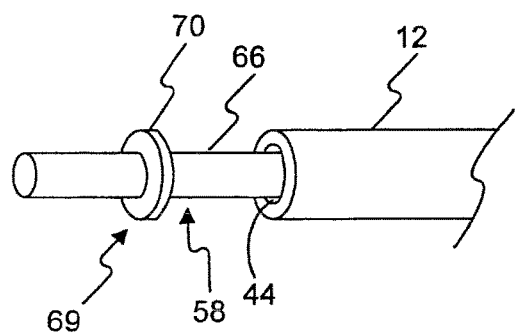
FIG. 20 is a handle of a medical retrieval device according to an embodiment of the present disclosure.

As shown in FIG. 20, a further embodiment of a laser fiber stop 69 may be a hard stop 70 connected to the outside of the laser fiber section 66 that includes the cladding. In this embodiment, the hard stop 70 may be positioned so as to limit the distance a laser fiber 58 may be inserted into the handle 12 of the device. The position of the hard stop 70 may correspond to the pre-determined distance preventing damage to the device 10. For example, hard stop 70 may be placed such that the laser fiber tip may not advance beyond the pre-determined distance from the basket tip 38. Similar to the embodiments discussed above, the hard stop 70 may have a larger diameter than an opening of the handle 12 and may mechanically stop the advancement of the laser fiber 58 into the center passage 44 of the device 10.

Figure 21:
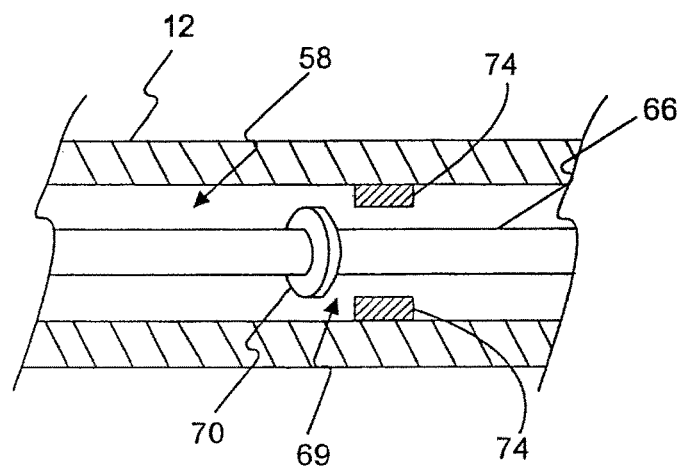
FIG. 21 is a cross-sectional view of a handle of a medical retrieval device according to an embodiment of the present disclosure.

FIG. 21 illustrates still another embodiment of the laser fiber stop 69 of the present disclosure. As shown, the laser fiber stop 69 may include hard stop 70 mounted to section 66 of the laser fiber 58 and may further include at least one handle stop 74 mounted to an inner surface of the handle 12. The handle stop 74 may be a single ring mounted to the handle 12 and may allow section 66 to pass through a hole in the center of the ring while mechanically stopping larger diameter hard stop 70. As in the embodiments described above, the laser fiber stop 69 of the present embodiment may be configured to limit the distance the laser fiber 58 may be inserted so as to prevent damage to the device 10.

Figure 22:
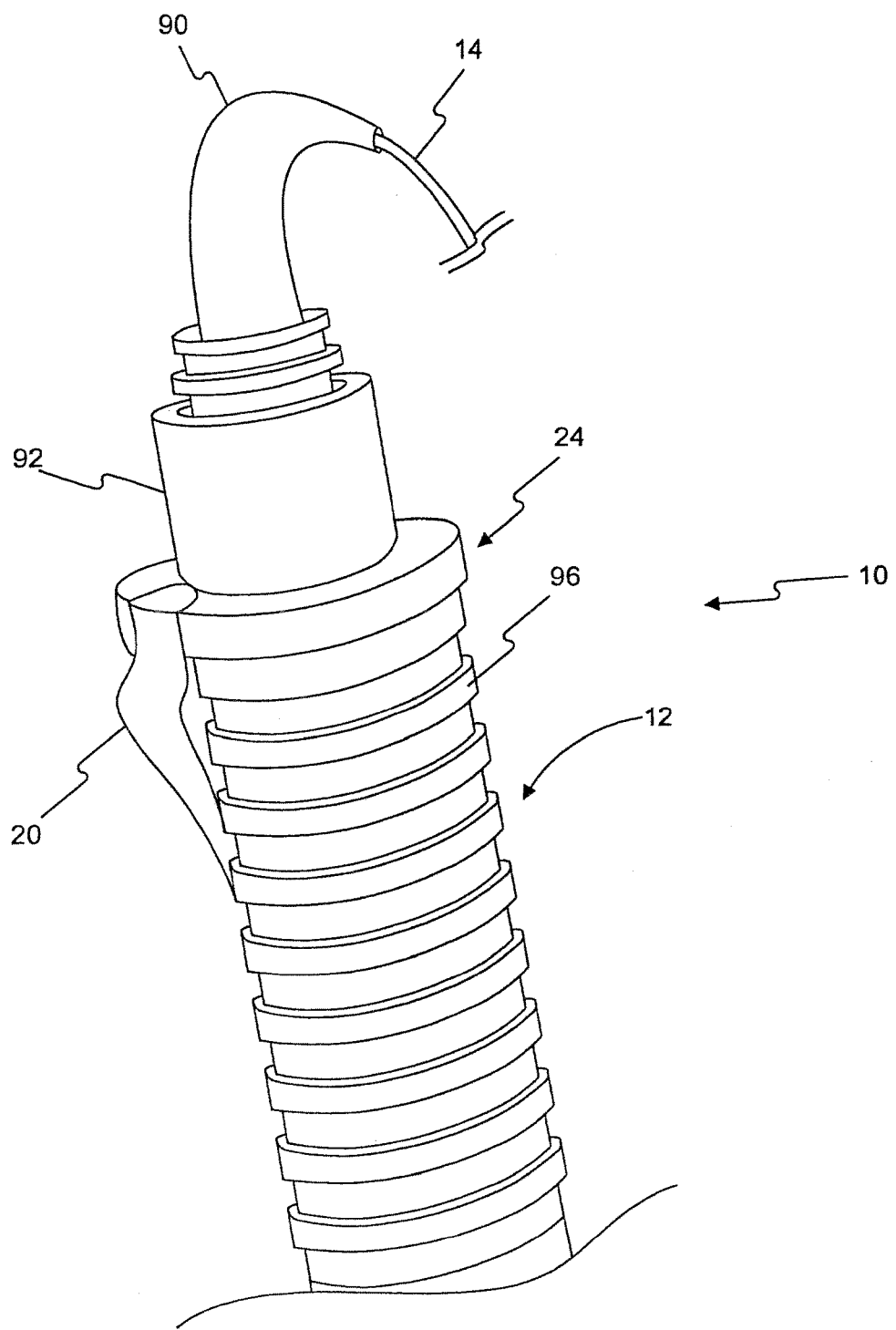
FIG. 22 is a portion of a medical retrieval device according to an embodiment of the present disclosure.

As discussed above, the device 10 of the present disclosure may include a handle 12, sheath 14, and handle cannula 76 (FIG. 1a). During operation of the device 10, the user may manipulate the handle 12 so as to cause at least part of the sheath 14 and/or handle cannula 76 to flex at a sharp angle relative to the handle 12. Such an angle is illustrated in FIG. 22. Manipulating the handle 12 in this way may cause at least one of these device elements to become deformed and/or permanently bent or damaged. For example, a bend in the handle cannula 76 may cause interference between the sheath 14 and the handle cannula 76 in subsequent cycles of use and may damage the sheath 14. Aspects of the present disclosure may be used in conjunction with the handle cannula 76 to avoid such damage during use.

For example, it may be desirable for the distal portion 80 of the handle cannula 76 to be relatively more flexible than the proximal portion 82 of the handle cannula 76. Such a configuration may allow for bending in the distal portion 80 and may enable the user to actuate the device 10 at any angle without permanently deforming the handle cannula 76 and/or damaging the integrity of at least the sheath 14.

Figure 23:
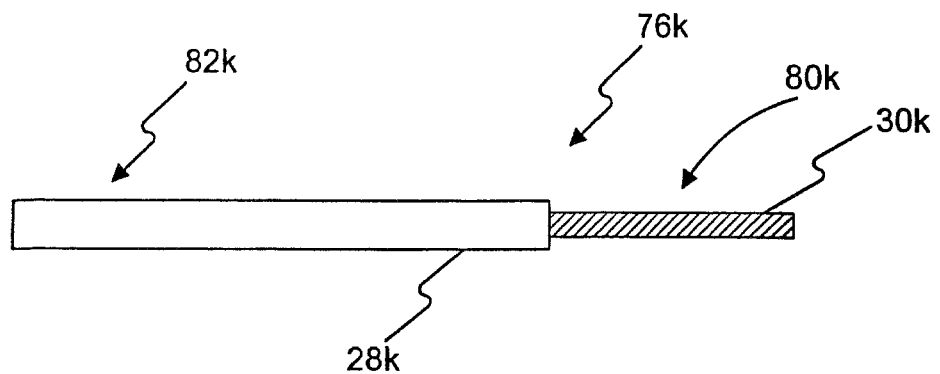
FIG. 23 is a handle cannula of a medical retrieval device according to an embodiment of the present disclosure.

In some embodiments of the present disclosure, the handle cannula 76 may be made of composite tube of the types and designs described throughout this disclosure. A composite tube handle cannula 76 may be substantially cylindrical and/or substantially hollow, and portions of the handle cannula 76 may be selectively removed through grinding, chemical etching, laser cutting, or other methods to create a desired strength or flexibility along portions of its length. For example, in some embodiments, the handle cannula 76 may include a stainless steel outer sleeve 28 and a hollow nitinol core 30. As shown in FIG. 23, a portion of a distal portion 80k of the handle cannula 76k may be removed to increase the flexibility of the distal portion 80k and allow for more acute bending. At least part of the outer sleeve 28k may be removed depending on the desired characteristics of the resulting handle cannula 76k. Thus, in the present embodiment, most of the stainless steel outer sleeve 28k may be removed to expose the more flexible nitinol core 30k.

Figure 24:
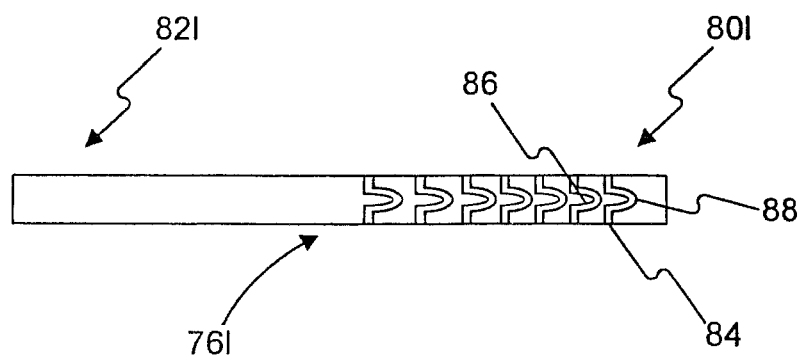
FIG. 24 is a handle cannula of a medical retrieval device according to another embodiment of the present disclosure.

As shown in FIG. 24, in other embodiments of the present disclosure, portions of the handle cannula 76l may be ground, chemically etched, laser cut, or otherwise removed so as to form a series of interconnected flexible discrete segments 84. Handle cannula 76l of this embodiment may include a cannula or tube with or without an inner core. The tube may be made of stainless steel or other suitable materials. In embodiments that include an inner core 30, the segments 84 may be formed of the outer sleeve of the handle cannula 76l and may be connected through a cooperatively linked engagement between adjacent discrete sections 84. Each segment 84 may include a convex protruding portion 86 on one end and a concave receiving portion 88 on another end. Adjacent segments 84 may be cooperatively linked by the engagement of adjacent convex protruding portions 86 and concave receiving portions 88. In addition, this linked engagement between discrete segments 84 permits pivoting movement of segments 84 relative to each other. FIG. 24 illustrates a series of segments in a linked engagement. It is contemplated that adjacent discrete segments 84 may be connected or engaged by suitable alternative designs other than the illustrated convex and concave portions 86, 88 so long as the segments 84 remain engaged and moveable relative to one another.

The discrete segments 84 may be located at approximately the distal-most two inches of the handle cannula 76. The segments 84 may create a desired strength or flexibility along the length of the handle cannula 76 corresponding to the location of the segments 84. For example, the formation of the segments 84 may remove at least a portion of a stainless steel outer sleeve 28 of a handle cannula 76. Thus, the formation of the segments 84 may expose at least a portion of, for example, a more flexible nitinol core 30 and may increase the flexibility of that portion of the handle cannula 76. The additional flexibility imparted may reduce or eliminate damage to the device 10 irrespective of the manner in which the handle 12 is manipulated.

In another embodiment, the handle cannula 76 may be a uniform tube or other like structure and may not include more than one material. Thus, the handle cannula 76 may not include, for example, at least two distinct layers of different material. In such an embodiment, the series of interconnected flexible discrete segments 84 may be ground, chemically etched, laser cut, or otherwise formed into the handle cannula 76 substantially as described above. The segments 84 may impart mechanical characteristics to the handle cannula 76 similar to those already explained.

Other embodiments of the invention will be apparent to those skilled in the art from consideration of the specification and practice of the invention disclosed herein. For example, the basket 16 may also include webbing, netting, or any other retrieval material disposed between at least a portion of at least two of the basket legs 18. The retrieval material may be polyvinyl alcohol ("PVA"), PTFE, EPTFE, PVE, foam, or any other polymer or composite known in the art. The retrieval material may also protect the legs 18 during stone reduction processes such as, for example, laser lithotripsy. In addition, the sheath 14 may include a number of flexible discrete segments 84. The flexible discrete segments 84 may further increase the flexibility of the sheath 14. The flexible discrete segments 84 may also increase the maneuverability of the device 10 while the device 10 is within the body of the patient.

It is intended that the specification and examples be considered as exemplary only, with a true scope and spirit of the invention being indicated by the following claims.

What is claimed is:

1. A medical retrieval device, comprising:
   a sheath defining a lumen;
   a retrieval assembly including a collapsed position within the lumen and an expanded position outside the lumen, the retrieval assembly connected to a shaft positioned in the lumen of the sheath; and
   a handle having a proximal end and a distal end, the distal end of the handle being coupled to a proximal end of the sheath, wherein the handle includes:
      an outer handle housing defining a lumen therein and longitudinally fixed relative to an inner sleeve and the shaft, wherein a proximal end of the inner sleeve extends proximally of the outer handle housing and at least a portion of the inner sleeve and the shaft are received within the lumen of the outer handle housing;
      a handle cannula extending through a lumen of the inner sleeve; and
      a slide having a first portion received radially within the outer handle housing and a second portion extending distally of the outer handle housing, the slide being movable relative to the handle cannula and the shaft;
      wherein at least a portion of the inner sleeve is positioned within a lumen of the slide.

2. The device of claim 1, wherein a portion of the handle cannula is located radially within the slide.

3. The device of claim 1, wherein a proximal end of the retrieval assembly is connected to a distal end of the shaft.

4. The device of claim 1, wherein the handle causes relative movement between the shaft and the sheath.

5. The device of claim 1, wherein the handle cannula is made of composite wire.

6. The device of claim 1, wherein the shaft is tubular.

7. The device of claim 6, wherein the shaft is configured to moveably receive a laser fiber therein.

8. A system, comprising:
   a sheath defining a lumen;
   a retrieval assembly including a collapsed position within the lumen and an expanded position outside the lumen, the retrieval assembly connected to a tubular shaft positioned in the lumen of the sheath;
   a handle having a proximal end and a distal end, the distal end of the handle being coupled to a proximal end of the sheath, wherein the handle includes:
      an outer handle housing defining a lumen therein and longitudinally fixed relative to an inner sleeve and the shaft, wherein at least a portion of the inner sleeve is positioned within the lumen of the outer handle housing;
      a handle cannula extending through a lumen of the inner sleeve and to a proximal end of the inner sleeve; and
      a slide at least partially received radially within the outer handle housing, the slide being movable relative to the handle cannula and the shaft; and
   a laser fiber moveably positioned within the shaft between a retracted configuration and an extended configuration; and
   wherein in the expanded position of the retrieval assembly, a proximal end face of the slide is positioned proximally of a distal end of the inner sleeve.

9. The system of claim 8, wherein the shaft includes a radially inwardly projecting abutment surface abutting a portion of the laser fiber in the extended configuration.

10. The system of claim 9, wherein the portion of the laser fiber includes a transition portion of the laser fiber, wherein the transition portion is disposed between a proximal portion having a first dimension and a distal portion having a second dimension.

11. The system of claim 10, wherein the second dimension is smaller than the first dimension.

12. The system of claim 8, wherein a portion of the handle cannula is located radially within the slide.

13. The system of claim 8, wherein a proximal end of the inner sleeve extends proximally of the outer handle housing.

14. The system of claim 8, wherein a proximal end of the retrieval assembly is connected to a distal end of the shaft.

15. A medical retrieval device, comprising:
   a sheath defining a lumen;
   a retrieval assembly including a collapsed position within the lumen and an expanded position outside the lumen, the retrieval assembly connected to a shaft positioned in the lumen of the sheath; and
   a handle having a proximal end and a distal end, the distal end of the handle being coupled to a proximal end of the sheath, wherein the handle includes:
      an outer handle housing longitudinally fixed relative to an inner sleeve and the shaft, wherein a proximal end of the inner sleeve extends proximally of the outer handle housing and at least a portion of the inner sleeve abuts a proximal end face of the outer handle housing;
      a handle cannula extending from a location proximal of the outer handle housing, through a lumen of the inner sleeve, and distally of the inner sleeve; and
      a slide extending distally of the outer handle housing, the slide being movable relative to the handle cannula and the shaft; and
      wherein in the expanded position of the retrieval assembly, an end face of the slide and the proximal end face of the outer handle housing are coplanar.

16. The device of claim 15, wherein a portion of the handle cannula is located radially within the slide.

17. The device of claim 15, wherein a proximal end of the retrieval assembly is connected to a distal end of the shaft.

18. The device of claim 15, wherein the handle causes relative movement between the shaft and the sheath.

19. The device of claim 15, wherein the shaft is tubular.

20. The device of claim 19, wherein the shaft is configured to moveably receive a laser fiber therein.

* * * * *